United States Patent
Serban et al.

(10) Patent No.: US 7,695,993 B2
(45) Date of Patent: Apr. 13, 2010

(54) MATRIX NANOCOMPOSITE SENSING FILM FOR SAW/BAW BASED HYDROGEN SULPHIDE SENSOR AND METHOD FOR MAKING SAME

(75) Inventors: Bogdan-Catalin Serban, Bucharest (RO); Stefan I. Voicu, Bucharest (RO); Stefan-Dan Costea, Bucharest (RO); Cornel P. Cobianu, Bucharest (RO)

(73) Assignee: Honeywell International Inc., Morristown, NJ (US)

( * ) Notice: Subject to any disclaimer, the term of this patent is extended or adjusted under 35 U.S.C. 154(b) by 154 days.

(21) Appl. No.: 12/116,724

(22) Filed: May 7, 2008

(65) Prior Publication Data

US 2009/0280593 A1 Nov. 12, 2009

(51) Int. Cl.
  H01L 21/00 (2006.01)
  H01L 29/12 (2006.01)
  H01L 49/00 (2006.01)
  G01N 27/12 (2006.01)

(52) U.S. Cl. .................. 438/49; 73/31.06; 29/592.1; 977/748; 977/835; 257/E21.04; 252/62.3 V

(58) Field of Classification Search ............... 438/49; 29/592.1; 73/31.06; 977/748, 835; 257/E21.04
  See application file for complete search history.

(56) References Cited

U.S. PATENT DOCUMENTS

| | | | |
|---|---|---|---|
| 5,321,146 A * | 6/1994 | Royster et al. | 556/57 |
| 5,433,971 A * | 7/1995 | Royster et al. | 427/58 |
| 5,629,435 A * | 5/1997 | Royster et al. | 556/1 |
| 6,420,293 B1 | 7/2002 | Chang et al. | 501/95.2 |
| 2003/0099575 A1 * | 5/2003 | Sung et al. | 422/88 |
| 2006/0079626 A1 | 4/2006 | Curran et al. | 524/496 |
| 2006/0252853 A1 | 11/2006 | Ajayan et al. | 523/215 |
| 2008/0209876 A1 * | 9/2008 | Miller | 55/522 |
| 2009/0280031 A1 * | 11/2009 | Serban et al. | 422/83 |

OTHER PUBLICATIONS

Carbon Nanotubes as Polymer Antioxidants; P.C.P. Watts, P.K. Fearon, W.K. Hsu, N.C. Billingham, H.W. Kroto, D.R.M. Walton; The Royal Society of Chemistry 2003; J. Mater. Chem. 2003, 13, 491-495.

Nanocomposites Based on Conducting Polymers and Carbon Nanotubes from Fancy Materials to Functional Applications; M. Baibarac, P. Gomez-Romero; Journal of Nanoscience and Technology, vol. 6, 1-4, 2006.

(Continued)

*Primary Examiner*—Evan Pert
(74) *Attorney, Agent, or Firm*—Kris T. Fredrick; Kermit D. Lopez; Luis M. Ortiz

(57) ABSTRACT

A method can be adapted for design and preparation of a matrix nanocomposite sensing film for hydrogen sulphide SAW/BAW detection at room temperature. A matrix nanocomposite can be synthesized by incorporating both single-wall and multi-wall thiolated carbon nanotubes into conductive organic polymers or ceramic nanocrystalline in a properly functionalized manner. A thin organic sensing film can be prepared based on the matrix nanocomposite. The matrix nanocomposite sensing film can be prepared on a surface of a SAW/BAW device by an additive process or a direct printing process. Finally, the sensing film can be consolidated by thermal annealing or laser annealing under ambient conditions in order to obtain the stable sensing film with higher sensitivity and electrical properties for a SAW/BAW based $H_2S$ sensor.

20 Claims, 6 Drawing Sheets

OTHER PUBLICATIONS

Preparation of Polythiophene Composite Film by in Situ Polymerization at Room Temperature and its Gas Response Studies; X. Ma, G. Li, H. Xu, M. Wang, H. Chen; www.sciencedirect.com; Thin Solid Films, 515 (2006) 2700-2704.

Linear Ladder-Type π-Conjugated Polymers Composed of Fused Thiophene Ring Systems; K. Oyaizu, T. Iwasaki, Y. Tsukahara, E. Tsuchida; Macromolecules 2004, 37, 1257-1270.

Synthesis and Characterization of Conducting Polythiophene/Carbon Nanotubes Composites; M. R. Karim, C.J. Lee, M.S. Lee; www.interscience.wiley.com.

Synthesis and Properties of Poly[3-(ω-bromoalkyl) thiophene]; m. Pomerantz, M. L. Liu; Elsevier Science; Synthetic Metals 101 (1999) 95.

Properties and Mechanism Study of Ag doped $SnO_2$ thin films as $H_2S$ Sensors; C.H. Liu, L. Zhang, Y-J. He, Elsevier Science; Thin Solid Films 304 (1997) 13-15.

Surface-Acoustic-Wave-Enhanced Alignment of Thiolated Carbon Nanotubes on Gold Electrodes; T. Smorodin, U. Beierlein, J. Ebbecke, A. Wixforth; www.interscience.wiley.com; 2005, 1, No. 12, 1188-1190.

Fullerene Pipes; Jie Liu, et al., Science 280, 1253 (1998); DOI: 10.1126/science.280.5367.1253.

Selective Thiolation of Single-Walled Carbon Nanotubes; J.K. Lim, W.S. Yun, M. Yoon, S. K. Lee, C.H. Him, K. Kim, S.S. Kim; Elsevier Science, Synthetic Metals 139 (2003) 521-527.

$H_2S$ Sensing Properties of the SnO2 Based Thin Films; L. Jianping, W. Yue, G. Xiaoguang, M. Qing, W. Li, H. Jinghong; Elsevier Science, Sensors and Actuators B 65 (2000) 111-113.

$H_2S$ Detection Sensing Characteristic of $CuO/SnO_2$ Sensor; J. Liu, X. Huang, G. Ye, W. Liu, Z. Jiao, W. Chao, Z. Zhou, Z. Yu; Sensors 2003, 3, 110, 118.

Hydrogen Sulfide Surface Acoustic Wave Gas Detector; J. F. Vetelino, R.K. Lade, R.S. Falconer; IEEE Transactions and Ultrasonics, Ferroelectrics, and Frequency Control, vol. UFFC-34, No. 2, Mar. 1987.

* cited by examiner

US 7,695,993 B2

MATRIX NANOCOMPOSITE SENSING FILM FOR SAW/BAW BASED HYDROGEN SULPHIDE SENSOR AND METHOD FOR MAKING SAME

TECHNICAL FIELD

Embodiments are generally related to solid-state sensors for hydrogen sulphide detection. Embodiments are particularly related to a matrix nanocomposite sensing film and method for its preparation. Embodiments are additionally related to a SAW/BAW based hydrogen sulphide sensor with the matrix nanocomposite sensing film.

BACKGROUND OF THE INVENTION

Hydrogen sulphide ($H_2S$) is a flammable, irritating, corrosive, typically bad-smelling and extremely toxic gas. Toxicity of the hydrogen sulphide is comparable with hydrogen cyanide, which is considered as a broad-spectrum poison. Hydrogen sulphide can affect different parts and systems such as skin, eyes and throat in the human body, depress the nervous system and eventually cause death. Hydrogen sulphide occurs naturally in the environment, but ultra low levels can be tolerated because the human body can possess a number of enzymes that are able to perform the conversion through oxidation of hydrogen sulphide to sulphate.

It is important to continually sense the hydrogen sulphide to provide safeguards for the employees who work in areas like petrochemical and fuel refinery industry where hydrogen sulphide exists. The detection of hydrogen sulphide is also very beneficial for the biomedical field, especially for determination of $H_2S$ content in mouth air and for diagnosis in dentistry. Semiconductor oxides play a significant role for $H_2S$ sensing. Tin dioxide-based materials such as pure $SnO_2$, $CuO$—$SnO_2$ and $SnO_2$—$Ag_2O$ can easily sense $H_2S$ in air. Copper oxide is a best promoter for the $SnO_2$-based hydrogen sulphide sensors. However, such sensors exhibit the maximum sensitivity at elevated temperatures, (i.e. around 150° C.). At this elevated temperature, irreversible reactions can take place between the gas and the sensing layer, which affects the long-term stability of the sensor.

Some prior art gas sensors utilize a thin solid film on a SAW/BAW device to overcome the aforementioned drawbacks. In such gas sensors, gas molecules are adsorbed onto the surface of solid film due to the interactions like hydrogen bond, electrostatic, pi-pi stacking, Van Der Waals and host-guest relationships. Therefore, the propagation velocity of the SAW/BAW acoustic waves can be alerted and eventually a shift in the phase or resonance frequency of SAW/BAW devices is induced, as a function of the gas. Sputtered inorganic film based on activated tungsten trioxide materials, (e.g. pure tungsten trioxide, doped tungsten trioxide with iridium, gold and palladium), can be developed to form a sensitive film for hydrogen sulphide detection. Such thin films exhibit a good sensitivity toward hydrogen sulphide, but unfortunately the temperature still remains too high, (i.e. around 130° C.).

Furthermore, single-wall and double-wall carbon nanotubes, well known as inert molecules, have been utilized to form the sensing film, but the manipulation of carbon nanotubes exhibits important disadvantages such as low solubility and difficult chemical and physical processing. In addition, covalent and noncovalent functionalization of the carbon nanotubes diminishes the inertness property. The most popular covalent functionalization involves sonication of carbon nanotubes in a mixture of concentrated nitric acid/sulphuric acid, which oxidizes the parent molecule and introduces different groups onto the surface of carbon nanotubes such as carboxyl (—COOH), hydroxyl (—OH) and carbonyl (—C═O). Also, amino carbon nanotubes are available through the intermediate of Curtius transposition or Hoffmann degradation. Therefore, such single-wall and multi-wall carbon nanotubes are functionalized with mercapto groups (—SH) to overcome such disadvantages.

In addition, the functionalization of the molecular architecture of carbon nanotubes has been developed for the synthesis of CNT—CO—NH—$(CH_2)$11-SH. This derivatization involves sonication of carbon nanotubes in nitric acid/sulphuric acid mixture, the addition of thionil chloride to convert carboxylic groups to the corresponding acid chloride, and treatment with α, ω mercapto-amine bifunctional compound to produce the alkanethiol. It has been shown that the mercapto-group is located at the end of alkylic chain with eleven carbon atoms, and that the mercapto-amide groups form a bridge between parent carbon nanotube and alkanethiol. Additionally, a selective thiolation of carbon nanotubes is the synthesis of CNT—$CH_2$—SH, which involves sonication of carbon nanotubes in nitric acid/sulphuric acid mixture for 24 hour to introduce carboxylic groups at the surface of CNTs, and treatment of carboxylic CNTs with sodium borohydride to split carboxylic group into alcoholic groups. The synthesis of CNT—$CH_2$—SH also involves conversion of alcoholic groups to the corresponding chloride groups, and finally treatment of the chloromethylated carbon nanotubes into mercapto methylated CNTs during the reaction with thiourea. The single wall carbon nanotubes can also be functionalized with cysteamine molecules.

In the majority of prior art, the link between carboxylic nanotubes and amine group in cysteamine can be performed using a carbodiimide as a catalyst, (i.e. 1-ethyl-1,3-[3 dimethylaminopropyl]carbodiimide hydrochloride). Recently, conductive organic polymers can be used to prepare organic compounds based sensing films with versatile applications such as gas sensors, solar cells, batteries, antistatic coatings, electro-luminescent devices, electrodes, nonlinear optical devices, transistors, etc. Polythiophene (PT) is an organic polymer, which exhibits high environmental stability, facile routes of chemical or electrochemical synthesis and functionalization, and thermal stability. A variety of derivatives of polythiophenes can be synthesized in the form of poly(3-butylthiophene), poly(3-hexylthiophene), poly(3-octylthiophene), poly(3-thiophenealkanesulfonate), poly(3-dodecylthiophene), and poly(3-perfluorooctylthiophene). Such polythiophene can be functionalized with macrocyclic cavities of crown ethers for detection of metal ions. The polythiophene is also functionalized with chiral primary amine for separation of chiral species, especially chiral amino alcohols. Recent publications relate the synthesis of poly[3-(6-bromohexylthiophene)] and poly[3-(12-bromododecylthiophene)], two types of poly[3(ω-bromoalkylthiophene)] which offer a myriad of ways for new functionalizations through the intermediate of displacement reactions. Synthesis of a novel compound, thieno[n]acene, was also reported. Composite polythiophene/boron trifluoride etherate was used to prepare sensitive film for detection of the following vapors: n-hexane, ammonia, triethylamine, acetone, water, trimethylamine, toluene, alcohols. The sensitivity response is proportional with the polarity of tested vapors. Even such combinations of the polythiophene and the carbon nanotubes often lack in $H_2S$ sensitivity, and mechanical and electrical properties. Hence, it is desirable to manufacture miniaturized solid-state sensors with increased performance for $H_2S$ sensing.

A need therefore exists for an improved method for the design and preparation of a matrix nanocomposite-based sensing film with high sensitivity, which enables hydrogen sulphide SAW/BAW detection at room temperature. Such an improved method is described in greater detail herein.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide an improved method for the design and preparation of a matrix nanocomposite sensing-based film containing thiolated carbon nanotubes or a network of thiolated carbon nanotubes.

It is another aspect of the present invention to provide a SAW/BAW based hydrogen sulphide sensor with the matrix nanocomposite sensing-based film.

The aforementioned aspects and other objectives and advantages can now be achieved as described herein. An improved method for design and preparation of a matrix nanocomposite-based sensing film for hydrogen sulphide SAW/BAW detection at room temperature is provided. A matrix nanocomposite can be synthesized by incorporating both single-wall and multi-wall thiolated carbon nanotubes into conductive organic polymers or ceramic nanocrystalline in a properly functionalized manner. A thin organic sensing film can be prepared based on the matrix nanocomposite. The matrix nanocomposite sensing film can be obtained by starting from a solution in which the matrix nanocomposite is homogenously dispersed and following with its deposition on a surface of a SAW/BAW device by an additive process or by a direct printing process. Finally, the sensing film can be consolidated by thermal annealing or laser annealing under ambient conditions in order to obtain the stable sensing film with higher sensitivity and electrical properties for a SAW/BAW based $H_2S$ sensor.

Furthermore, in accordance with other aspects of the present invention, the thiolated carbon nanotubes can also be incorporated in a ceramic nanocrystalline to form ceramic nanocomposites. Such ceramic nanocomposites based sensing films are widely utilized in different areas such as high temperature gas sensors, gas turbines, automotive applications, etc. Three types of thiolated carbon nanotubes can be utilized for design and preparation of the matrix nanocomposites. Such carbon nanotubes can include mercapto groups or functional groups such as thioester.

The matrix nanocomposites can be designed based on polythiophene with a mercapto group situated at the end of alkylic chain and thiolated carbon nanotubes, based on polythiophene derivative functionalized with methylene mercapto carbon nanotubes and thiolated carbon nanotubes, and based on thiolated carbon nanotubes and tungsten trioxide. Thus, the sensitivity of the matrix nanocomposites-based sensing films toward $H_2S$ at room temperature is improved by the presence of mercapto groups, thioethers groups and thioesters groups, and by the presence of sulfur atoms in the polymers. The thin sensing films made up of such matrix nanocomposites can therefore achieve effective detection of hydrogen sulphide at room temperature.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

The present embodiment can utilize three types of thiolated carbon nanotubes such as thiolated carbon nanotube with mercapto groups connected to the tubular structure through one methylene group, (i.e. $CNT-CH_2-SH$), thiolated carbon nanotubes with the linkage between the CNT and alkane thiol by a amide group, (i.e. $CNT-CO-NH(CH_2)-SH$), and a network of two thiolated carbon nanotubes with the thioester group, (i.e. $CNT-CH_2-S-CS-CNT$). The thiolated carbon nanotubes or network of thiolated carbon nanotubes can be incorporated into polymeric materials or in a ceramic nanocrystalline to form matrix nanocomposites. The polymers which are used are: poly[3-(6-mercaptohexyl)thiophene], poly[3-(12-mercaptododecyl)thiophene], poly[3-(12-mercaptododecyl)thiophene] functionalized with methylene carbon nanotubes, poly[3-(6-mercaptohexyl)thiophene] functionalized with methylene carbon nanotubes, and thienoacene.

The carbon nanotubes with mercapto groups are single-wall or multi-wall. Similarly, the polymers are conductive polymers with polar structures and contain sulfur atoms in different ratios. Both single-wall and multi-wall carbon nanotubes can be incorporated in the conductive organic polymers to yield the matrix nanocomposites solid sensing film with good electrical and mechanical properties. The matrix nanocomposites contain both polymers and carbon nanotubes in different proportions. Thus, mechanical properties of nanocomposites solid films can be improved due to the remarkable mechanical properties of carbon nanotubes. Similarly, electrical properties of the organic polymer can be changed due to the π-π (pi-pi) stacking interactions between aromatic rings of the carbon nanotubes and the polymers. The sensitivity of the matrix nanocomposites-based sensing layers toward $H_2S$ at room temperature can also be improved by the presence of mercapto groups, thioethers groups and thioesters groups, and by the presence of sulfur atoms present in the organic polymers.

Figure 1:
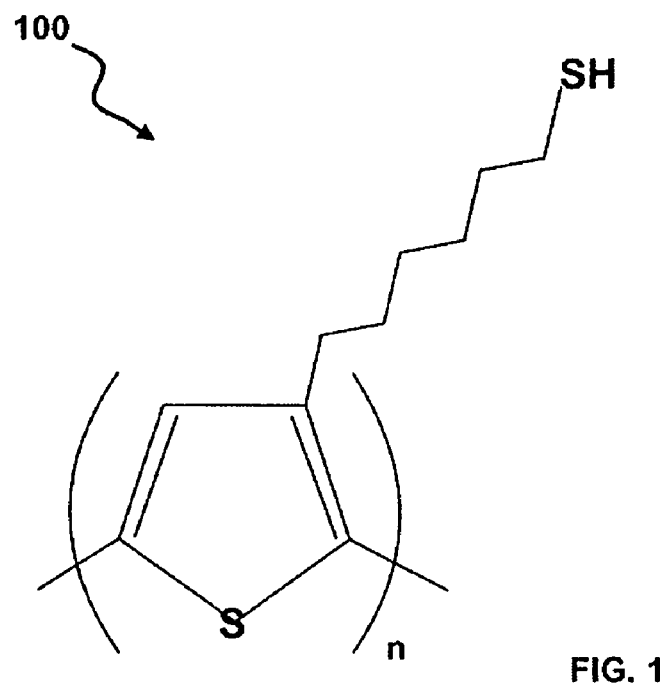
FIG. 1 illustrates a structure of poly[3-(6-mercaptohexyl)thiophene], which can be adapted for use in implementing a preferred embodiment.

Referring to FIG. 1, a structure 100 of poly[3-(6-mercaptohexyl)thiophene] is illustrated, which can be adapted for use in implementing a preferred embodiment. The structure 100 of poly[3-(6-mercaptohexyl)thiophene] can be utilized to design solid sensing layers based on matrix nanocomposites containing thiolated carbon nanotubes for being used as functionalized film in hydrogen sulphide surface acoustic wave (SAW)/bulk acoustic wave (BAW) detection. The design of matrix nanocomposites can be based on polythiophene with mercapto group situated at the end of alkylic chain and the thiolated carbon nanotubes. For example, the thiolated carbon nanotubes with the general formula CNT—$CH_2$—SH can be incorporated in the structure 100 of poly[3-(6-mercaptohexyl)thiophene], as shown in FIG. 1.

In order to form matrix nanocomposites, a solution of CNT—$CH_2$—SH, (i.e. 0.5 g in 200 ml chloroform), is subjected to sonication in an ultrasonical bath for 12 hours for performing a well dispersion of CNTs in a chosen solvent. Similarly, a solution of poly[3-(6-mercaptohexyl)thiophene] 100 can be prepared by dissolving 2 grams of polymer in 200 ml of toluene. Thereafter, both solutions are mixed and again subjected to sonication for 4 hours. At the end of the above mixture sonication, a homogeneous solution may be achieved. Finally, the homogeneous solution can be deposited onto the surface of piezoelectric quartz to obtain a gel-like layer. The thermal consolidation of the gel layer will finally determine a high quality thin solid sensing film. Normally, the nanocomposite poly[3-(6-mercaptohexyl)thiophene] 100, thiolated carbon nanotubes exhibit interaction of the carbon nanotubes with hydrogen sulphide molecules through dipoles-dipoles forces for $H_2S$ detection in the sensing layer of the SAW/BAW devices. Such carbon nanotubes contain antioxidant characteristics, which can increase the lifetime and mechanical properties of the polymers, and also diminish the strong humidity sensing property of the SAW/BAW sensors due to the hydrophobic character of the nanotubes.

Figure 2:
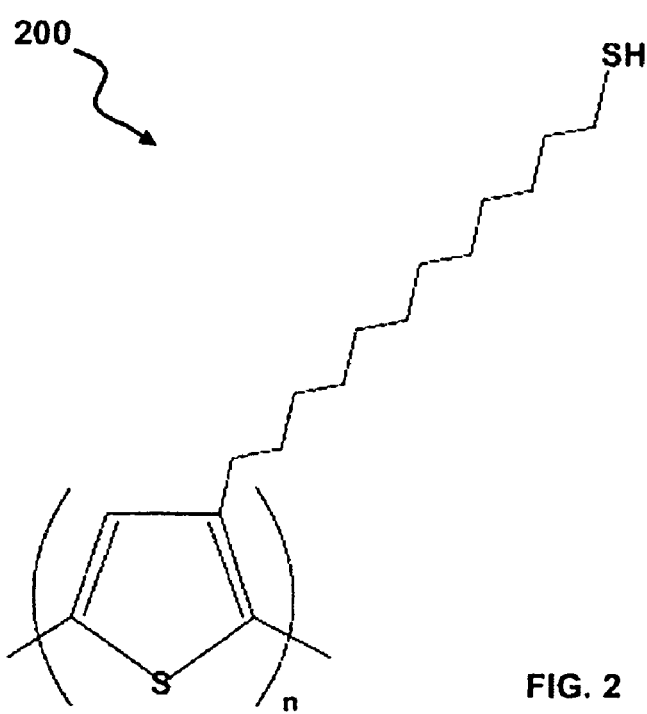
FIG. 2 illustrates a structure of poly[3-(12-mercaptododecyl)thiophene], which can be implemented in accordance with an alternative embodiment.

Referring to FIG. 2, structure 200 of poly[3-(12-mercaptododecyl)thiophene] is illustrated, which can be implemented in accordance with a feature of the present invention. The structure 200 of poly[3-(12-mercaptododecyl)thiophene] can also be mixed with the solution of CNT—$CH_2$—SH. Then the mixture solution can be further sonicated to obtain a matrix nanocomposite homogeneous solution to be used for the sensing film preparation. The next step is direct printing of the solution on the quartz surface. After printing, a gel-like layer is obtained, where a part of the solvent is evaporated. The following drying and thermal consolidation steps will remove all the solvents from the gel layer and finally will end up with achieving the solid sensing film.

Figure 3:
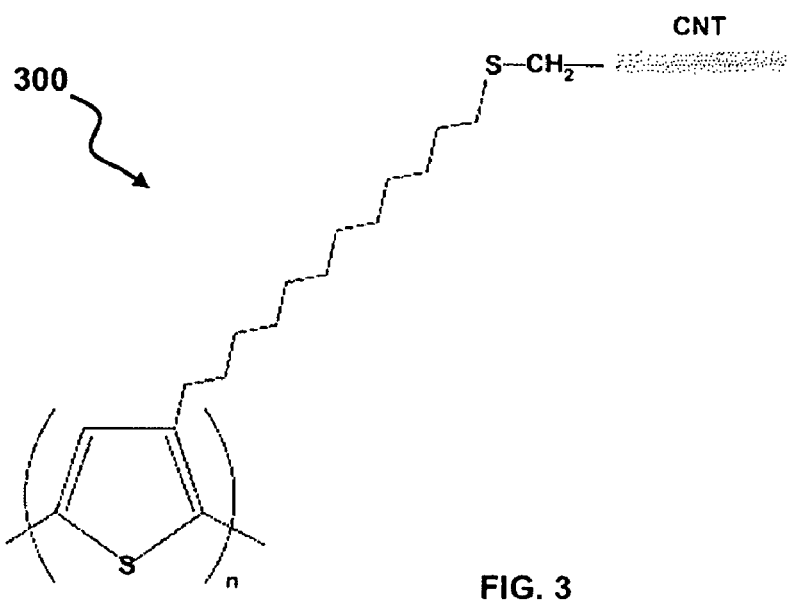
FIG. 3 illustrates a structure of poly[3-(12-mercaptododecyl)thiophene] functionalized with methylene carbon nanotubes, which can be implemented in accordance with an alternative embodiment.

Referring to FIG. 3, the structure 300 of poly[3-(12-mercaptododecyl)thiophene] functionalized with methylene carbon nanotubes is illustrated, which can be implemented in accordance with a feature of the present invention.

Figure 4:
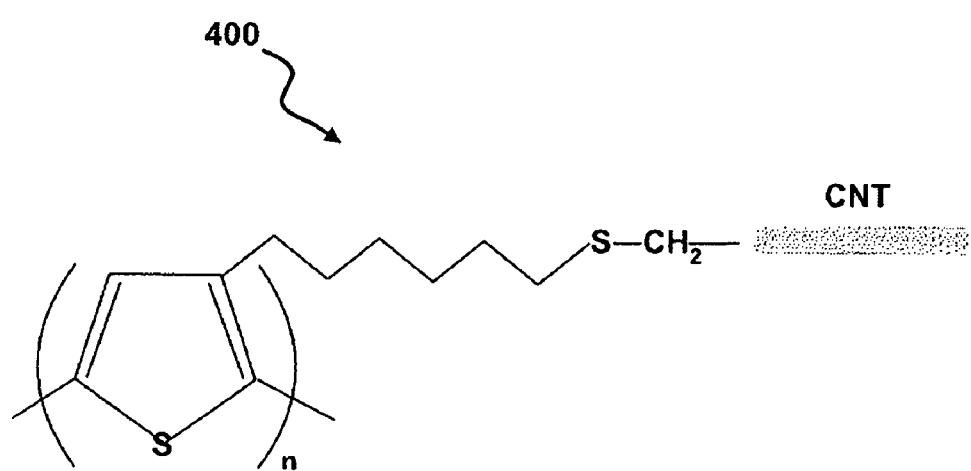
FIG. 4 illustrates a structure of poly[3-(6-mercaptohexyl)thiophene] functionalized with methylene carbon nanotubes, which can be implemented in accordance with an alternative embodiment.

Referring to FIG. 4, a structure 400 of poly[3-(6-mercaptohexyl)thiophene] functionalized with methylene carbon nanotubes is illustrated, which can be implemented in accordance with an alternative embodiment. The matrix nanocomposites-based sensing film can be prepared based on the structure 400 of poly[3-(6-mercaptohexyl)thiophene] functionalized with methylene mercapto carbon nanotubes and the thiolated carbon nanotubes for hydrogen sulphide SAW/BAW detection. The polythiophene derivative functionalized with methylene mercapto carbon nanotubes can be synthesized based on the reaction of poly[3-(6-bromohexyl)thiophene] in nucleophilic bimolecular displacement with thiolated carbon nanotubes or the reaction with chloromethyl carbon nanotubes.

For example, a solution of CNT—CO—NH—$(CH_2)11$—SH, (i.e. 0.5 g in 200 ml chloroform), can be subjected to sonication in an ultrasonical bath for 10 hours to perform a well dispersion of CNTs in a chosen solvent. Similarly, a solution of poly[3-(6-mercaptohexyl)thiophene] functionalized with methylene mercapto carbon nanotubes can be prepared in parallel by dissolving 3 grams of polymer in 200 ml of toluene. Then both solutions are mixed and again subjected to sonication for 6 hours. Finally, the solution can be prepared based on the incorporation of thiolated carbon nanotubes into the polymeric matrice of poly[3-(6-mercaptohexyl)thiophene] functionalized with methylene mercapto carbon nanotubes. Such solutions can be deposited onto the surface of piezoelectric quartz by different methods such as spin coating, drop casting and direct printing.

Furthermore, the matrix nanocomposites can also be prepared based on thiolated carbon nanotubes and nanocrystalline tungsten trioxide. Therefore, the tungsten trioxide powder can be mixed with thiolated carbon nanotubes in a 10/1 masic ratio. Then, the mixture can be dispersed in mixture of solvents, for example, isopropyl alcohol/ethanol 50/50 v/v, for sonication for 12 hours. After that, the final solution can be deposited onto the surface of piezoelectric quartz following the steps described above. The homogenous solution of ceramic matrix nanocomposited consisting of tungsten trioxide and carbon nanotubes can be used for preparing a sensitive solid film for detection of $H_2S$ in SAW devices, as described above.

Figure 5:
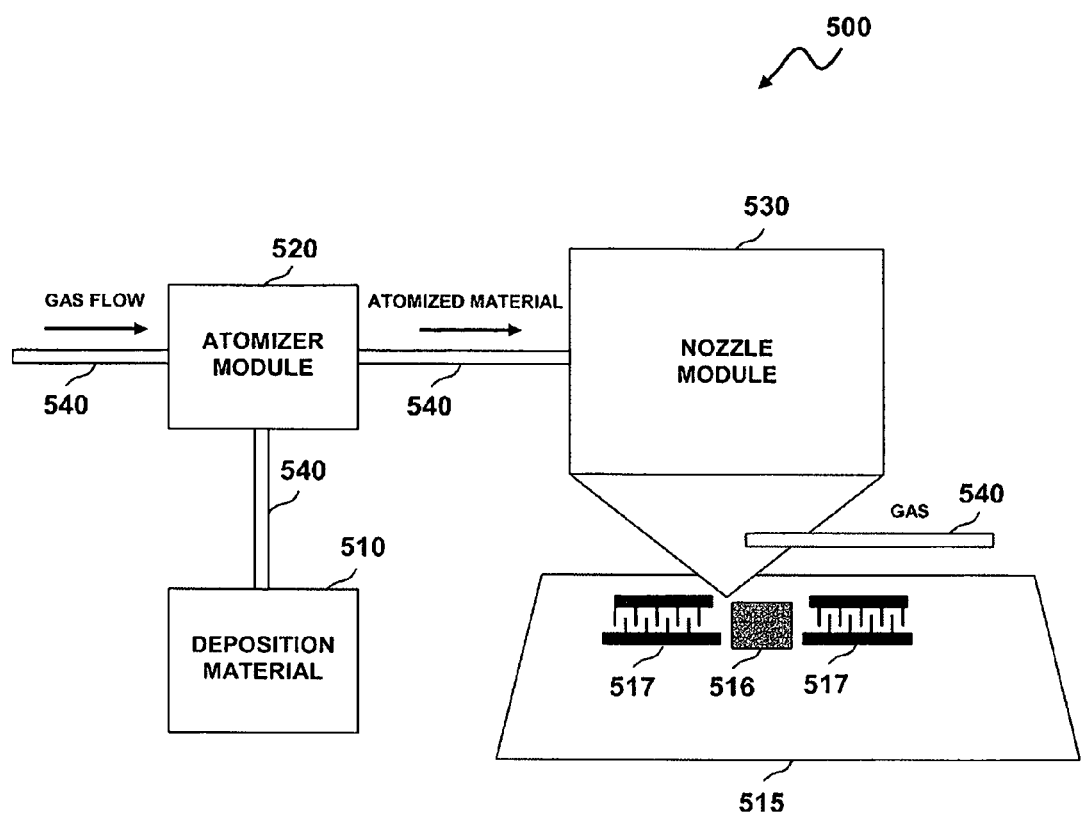
FIG. 5 illustrates a general schematic diagram of a system for the selective, maskless direct printing of a solution, which by thermal consolidation, will become a thin sensing film on a SAW device, which can be implemented in accordance with a preferred embodiment.

Referring to FIG. 5, a general schematic diagram of a system 500 for maskless, additive direct printing of a homogenous solution for preparing a thin sensing film 516 on a well defined zone of the SAW device is illustrated, which can be implemented in accordance with features of the present invention. The system 500 can include a module 510 containing a deposition material in liquid phase, an atomizer module 520 and a nozzle module 530. The deposition material can be a solution of matrix nanocomposites based on the polythiophene with mercapto group and the thiolated carbon nanotubes. The module 510 can supply the liquid deposition material to the atomizer module 520 via a supply tube 540 after synthesizing the homogeneous, segregation and particulate free solutions of matrix nanocomposites. The atomizer module 520 can transform the liquid phase of the desired deposition material into colloidal suspensions, (i.e. into the atomized material). Then the colloidal suspensions are transported to a nozzle module 530 with the help of carrier gas flow applied on the supply tube 540.

The nozzle module 530 can directly deposit well-controlled droplets of the deposition material onto a piezoelectric quartz substrate 515. The deposited polymer reaches a phase transition from the liquid phase to a gel state, when the deposition material can be applied on the piezoelectric quartz substrate 515. Then the gel state of the materials can be exposed to a heat treatment to dry and consolidate the thin polymer sensing film by removal of organic solvents from gel layer composition. The gel state of the materials can be consolidated and transitioned to a solid phase by thermal/laser annealing under the ambient conditions in order to achieve a stable sensing film 516 in both structural and functional manner. The gel state should be thermally treated by a laser treatment at the temperature allowed by the organic composition. The laser can be chosen in such a way that the bulk of energy can be absorbed in the sensing film 516.

Figure 6:
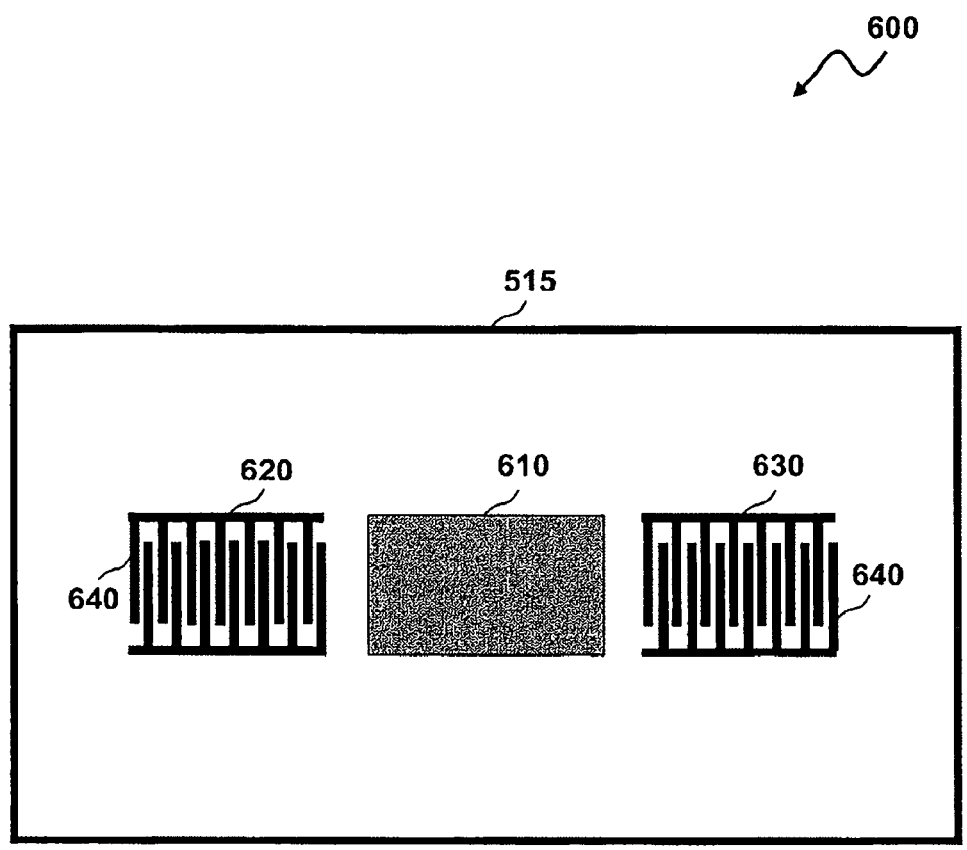
FIG. 6 illustrates a general schematic diagram of a delay line SAW chemical sensor with sensing layer located in a space between two interdigital transducers (IDT), which can be implemented in accordance with a preferred embodiment.

In addition, the stable sensing film 516 can be placed in between interdigital transducers 517, which acts as a SAW device, (i.e. SAW delay line-based chemical sensor 600, as shown in FIG. 6). The selective application of the liquid phase of the sensing film 516 in the specific regions of the solid state quartz substrate 515 can also be done by means of classical photoresist technology instead of the direct printing. Normally, the direct printing methods are utilized since the photoresist technology cannot provide an accurate selectivity during etching the organic sensing film 516 with respect to the photoresist masking layer (not shown). The direct printing methods exhibit a big advantage that the liquid material is printed only in the desired region of the quartz substrate 515. Thus, the amount of liquid material utilized for obtaining the solid sensing film 516 can be reduced.

Referring to FIG. 6, a general schematic diagram of a delay line SAW chemical sensor 600 with sensing layer 610 located in a space between two interdigital transducers (IDT) 620 and 630 is illustrated, which can be implemented in accordance with a preferred embodiment. The SAW chemical sensor 600 can be configured in a delay line configuration for $H_2S$ sensing, (i.e. the output signal of the SAW sensor 600 can be delayed relative to the input signal). The SAW chemical sensor 600 can include a thin sensing film or layer 610 and two interdigital transducers 620 and 630. In the delay line SAW sensor 600, the delay time is partially related to the amount of chemical sensed by the thin sensing layer 610. The delay time is also related to the spacing between the interdigital transducers 620 and 630. The thin sensing layer 610 can be designed based on polymeric or ceramic matrix nanocomposite with thiolated carbon nanotubes. The thin sensing layer 610 can be located in a space between the input interdigital transducer 620 and the output interdigital transducer 630 with the help of direct printing method.

The input and output interdigital transducers 620 and 630 are adapted to produce a different acoustic wavelength. The acoustic wavelength can be determined by a line width and spacing of interdigital electrode fingers 640 of each interdigital transducer 620 and 630. The interdigital electrode fingers 640 of each interdigital transducer 620 and 630 are electrically coupled via capacitive coupling. The interdigital electrode fingers 640 can be made from any suitable material such as aluminum (Al), platinum (Pt), gold (Au), rhodium (Rh), iridium (Ir), copper (Cu), titanium (Ti), tungsten (W), chromium (Cr) or nickel (Ni). The interdigital transducers 620 and 630 are formed on the piezoelectric quartz substrate 515. When an AC signal can be applied to the interdigital transducers 620 and 630, an electric field can be produced between the individual electrode fingers 640. Thus, the piezoelectric quartz substrate 515 exhibits the piezoelectric effect to cause a mechanical displacement such that the input interdigital transducers 620 can generate a surface acoustic wave in the piezoelectric quartz substrate 515.

Thereafter, the surface acoustic wave can pass the sensing layer 610, which can be adapted to selectively sense the hydrogen sulphide. The sensing layer 610 can interact with the hydrogen sulphide at room temperature by dipole-dipole forces. The shift in phase or frequency of the surface acoustic wave in the presence of the $H_2S$ gas takes place partly due to the loading device with $H_2S$ molecules and partly due to the changes in electro-visco-elastic properties of the matrix nanocomposites after exposure at the hydrogen sulphide. The output interdigital transducer 630 can receive the surface acoustic wave after passing the sensing layer 610. The output interdigital transducer 630 produces an output signal related to the amount of hydrogen sulphide sensed by the sensing layer 610 and in response to the received surface acoustic wave. The sensing layer 610 can accomplish two or more separate measurements, which results in increased accuracy and/or reliability for $H_2S$ sensing.

Figure 7:
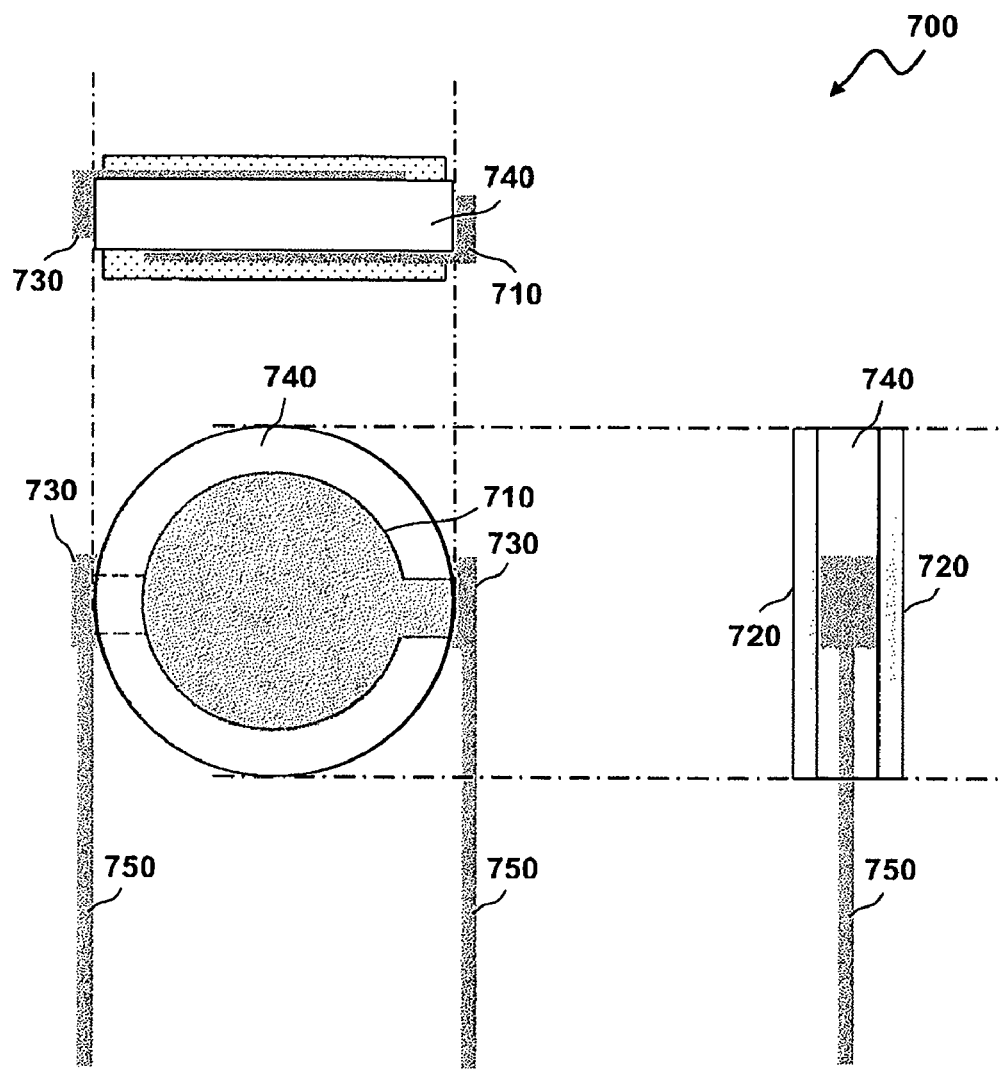
FIG. 7 illustrates a general schematic diagram of a BAW chemical sensor with sensing layer located on two sides of a BAW piezoelectric quartz substrate, which can be implemented in accordance with an alternative embodiment.

Referring to FIG. 7, a general schematic diagram of a BAW chemical sensor 700 with sensing layer located on two sides of a BAW piezoelectric quartz substrate 740 is illustrated, which said layer can be implemented by direct printing method in accordance with a feature of the present invention. The bulk acoustic wave (BAW) chemical sensor 700 consists of metal electrodes 710 and 730, a thin sensing layer 720, a BAW piezoelectric quartz substrate 740 and foils 750. The sensing layer 720 can be designed based on polymeric or ceramic matrix nanocomposite with thiolated carbon nanotubes. Such sensing layer 720 is located on both sides of the piezoelectric quartz substrate 740. A direct printing process can be adapted for selective application of the liquid solution of the sensing layer 720 on the surface of the piezoelectric quartz substrate 740.

In addition, the metal electrodes 710 and 730 can be affixed to the top and bottom of the piezoelectric quartz substrate 740. The foils 750 are connected to the metal electrodes 710 and 730 in order to provide electrical connections for the piezoelectric quartz substrate 740. The foils 750 can be any conductive material such as platinum or silver. The piezoelectric quartz substrate 740 can be held with silicone O-rings as shown in FIG. 7. The sensing layer 720 becomes sensitive from the hydrogen sulphide in the BAW chemical sensor 700 at room temperature. Therefore, the sensing layer 720 can sense any hydrogen sulphide in the air, which effects an equivalent mass change of the piezoelectric quartz substrate 740. Thus, the BAW chemical sensor 700 can effectively measure the change in the mass of the piezoelectric quartz substrate 740 in order to detect the strength of the hydrogen sulphide.

Figure 8:
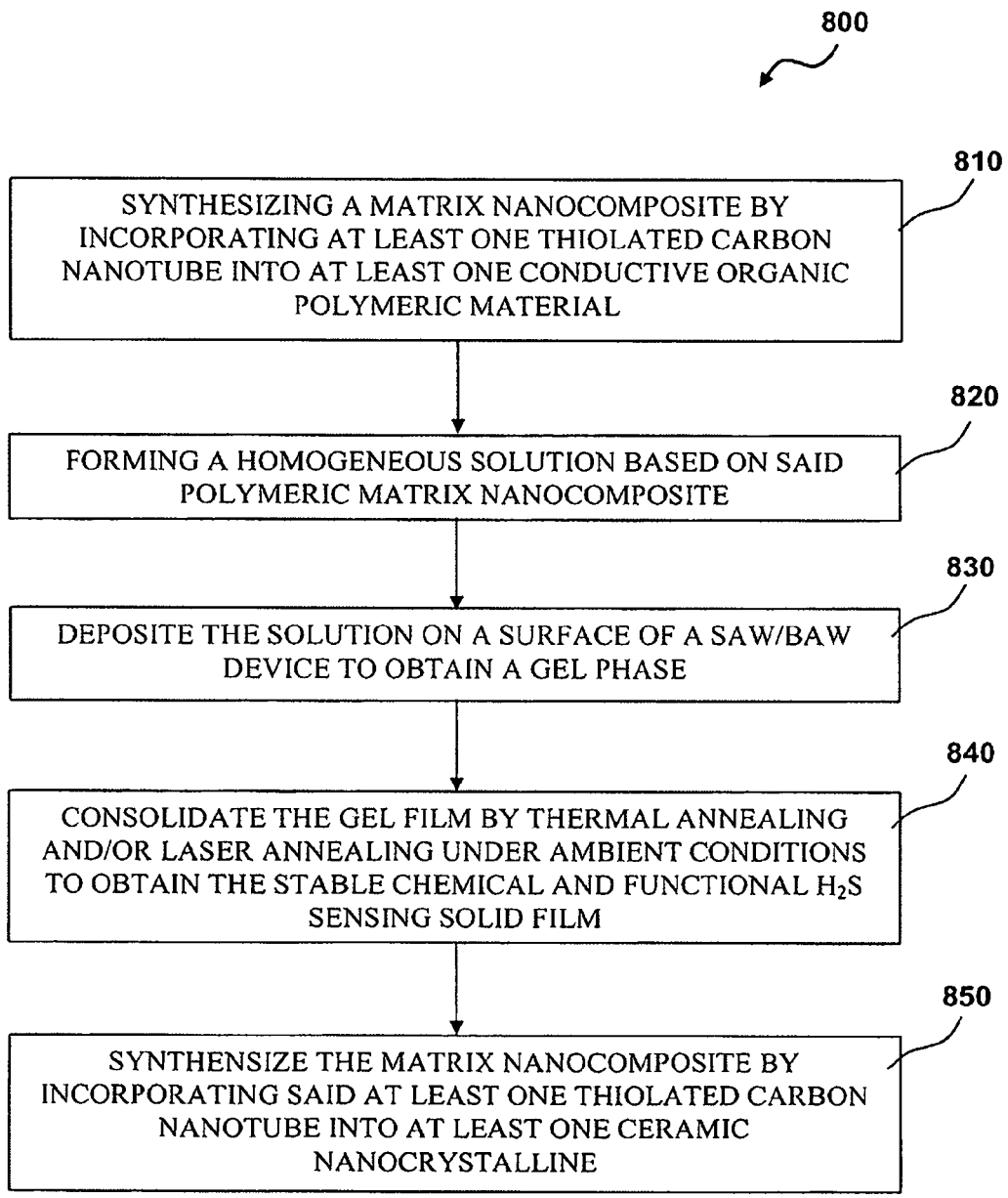
FIG. 8 illustrates a flow diagram of a method for preparing a matrix composite-based sensing film in accordance with the present invention.

Referring to FIG. 8, a flow diagram of a method for preparing a matrix nanocomposite sensing film is illustrated. First, referring to Block 810, a matrix nanocomposite is synthesized by incorporating at least one thiolated carbon nanotube into at least one conductive organic polymeric material. Then at least one thiolated carbon nanotube can comprise a mercapto group and a functional group such as thioester. Referring to Block 820, a homogenous solution acting as a precursor of the future thin sensing film can be formed based on said polymeric matrix nanocomposite. The homogenous solution from above can then be deposited on a surface of a SAW/BAW device by an additive process and/or a direct printing process, as shown in Block 830. Referring to Block 840, the thin gel film can be consolidated by thermal annealing and/or laser annealing under ambient conditions in order to obtain the stable chemical and functional $H_2S$ sensing thin solid film. The thin sensing film interacts with the hydrogen sulphide at room temperature by means of dipole-dipole forces. Referring to Block 850, the matrix nanocomposite can be synthesized by incorporating said at least one thiolated carbon nanotube into at least one ceramic nanocrystalline.

It will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

What is claimed is:

1. A method for preparing a matrix nanocomposite sensing film, comprising:
   synthesizing a matrix nanocomposite solution by incorporating at least one thiolated carbon nanotube into at least one conductive organic polymeric material, wherein said at least one thiolated carbon nanotube comprises a mercapto group and a functional group such as thioester;
   forming a thin gel film based on said polymeric matrix nanocomposite, by depositing said homogenous solution on a surface of a SAW/BAW device by an additive process and/or a direct printing process; and
   consolidating said thin gel film by thermal annealing and/or laser annealing under ambient conditions in order to obtain the stable chemical and functional $H_2S$ sensing thin solid film, wherein said thin sensing film interacts with the hydrogen sulphide at room temperature by means of dipole-dipole forces.

2. The method of claim 1, further comprising:
   synthesizing said matrix nanocomposite-containing solution by incorporating said at least one thiolated carbon nanotube into at least one ceramic nanocrystalline.

3. The method of claim 1 wherein said at least one conductive organic polymeric material comprises a poly[3-(6-mercaptohexyl)thiophene], a poly[3-(12-mercaptododecyl)thiophene], a poly[3-(6-mercaptohexyl)thiophene] functionalized with methylene carbon nanotubes, a poly[3-(12-mercaptododecyl)thiophene] functionalized with methylene carbon nanotubes, and a thienoacene.

4. The method of claim 1 wherein said at least one ceramic nanocrystalline comprises a tungsten trioxide.

5. The method of claim 1 wherein said at least one thiolated carbon nanotube comprises $CNT—CH_2—SH$, $CNT—CO—NH—(CH_2)11-SH$ and $CNT—CH_2—S—CS—CNT$.

6. The method of claim 1 wherein said at least one thiolated carbon nanotube comprises a single-wall carbon nanotube and a multi-wall carbon nanotube.

7. The method of claim 1 wherein said poly[3-(6-mercaptohexyl)thiophene] functionalized with methylene carbon nanotubes is synthesized from said poly[3-(6-mercaptohexyl)thiophene] and at least one chloromethylated carbon nanotube, and/or from a poly[3-(6-bromohexyl)thiophene] and said at least one thiolated carbon nanotube.

8. The method of claim 1 wherein said poly[3-(12-mercaptododecyl)thiophene] functionalized with methylene carbon nanotubes is synthesized from a poly[3-(6-mercaptododecyl)thiophene] and said at least one chloromethylated carbon nanotube, and/or from a poly[3-(12-bromododecyl)thiophene] and said at least one thiolated carbon nanotube.

9. A method for preparing a matrix nanocomposite sensing film, comprising:
   synthesizing a matrix nanocomposite solution by incorporating at least one thiolated carbon nanotube into at least one conductive organic polymeric material, wherein said at least one thiolated carbon nanotube comprises a mercapto group and a functional group such as thioester;
   forming a gel film based on said polymeric matrix nanocomposite by depositing said solution on a surface of a SAW/BAW device by an additive process and/or a direct printing process;
   consolidating said thin gel film by thermal annealing and/or laser annealing under ambient conditions in order to obtain the stable chemical and functional $H_2S$ sensing solid film, wherein said thin sensing film interacts with the hydrogen sulphide at room temperature by means of dipole-dipole forces; and
   synthesizing said matrix nanocomposite by incorporating said at least one thiolated carbon nanotube into at least one ceramic nanocrystalline.

10. The method of claim 9 wherein said at least one conductive organic polymeric material comprises a poly[3-(6-mercaptohexyl)thiophene], a poly[3-(12-mercaptododecyl)thiophene], a poly[3-(6-mercaptohexyl)thiophene] functionalized with methylene carbon nanotubes, a poly[3-(12-mercaptododecyl)thiophene] functionalized with methylene carbon nanotubes, and a thienoacene.

11. The method of claim 9 wherein said at least one ceramic nanocrystalline comprises a tungsten trioxide.

12. The method of claim 9 wherein said at least one thiolated carbon nanotube comprises $CNT—CH_2—SH$, $CNT—CO—NH—(CH_2)11-SH$ and $CNT—CH_2—S—CS—CNT$.

13. The method of claim 9 wherein said at least one thiolated carbon nanotube comprises a single-wall carbon nanotube and a multi-wall carbon nanotube.

14. The method of claim 9 wherein said poly[3-(6-mercaptohexyl)thiophene] functionalized with methylene carbon nanotubes is synthesized from said poly[3-(6-mercaptohexyl)thiophene] and at least one chloromethylated carbon nanotube, and/or from a poly[3-(6-bromohexyl)thiophene] and said at least one thiolated carbon nanotube.

15. The method of claim 9 wherein said poly[3-(12-mercaptododecyl)thiophene] functionalized with methylene carbon nanotubes is synthesized from a poly[3-(6-mercaptododecyl)thiophene] and said at least one chloromethylated carbon nanotube, and/or from a poly[3-(12-bromododecyl)thiophene] and said at least one thiolated carbon nanotube.

16. A matrix composite solution adapted for preparation of a sensing film, comprising at least one thiolated carbon nanotube synthesized into at least one conductive organic polymeric material, wherein said at least one thiolated carbon nanotube comprises a mercapto group and a functional group such as thioester on a surface of a SAW/BAW device.

17. The matrix composite of claim 16, wherein said at least one conductive organic polymeric material comprises a poly[3-(6-mercaptohexyl)thiophene], a poly[3-(12-mercaptododecyl)thiophene], a poly[3-(6-mercaptohexyl)thiophene] functionalized with methylene carbon nanotubes, a poly[3-(12-mercaptododecyl)thiophene] functionalized with methylene carbon nanotubes, and a thienoacene.

18. The matrix composite of claim 16, wherein said at least one ceramic nanocrystalline comprises a tungsten trioxide.

19. The matrix composite of claim 16, wherein said at least one thiolated carbon nanotube comprises $CNT—CH_2—SH$, $CNT—CO—NH—(CH_2)11-SH$ and $CNT—CH_2—S—CS—CNT$.

20. The matrix composite of claim 16, wherein said at least one thiolated carbon nanotube comprises a single-wall carbon nanotube and a multi-wall carbon nanotube.

* * * * *